United States Patent [19]

Bittner

[11] Patent Number: 4,536,895

[45] Date of Patent: Aug. 27, 1985

[54] VAULTED INTRAOCULAR LENS

[75] Inventor: Timothy Bittner, Duarte, Calif.

[73] Assignee: Ioptex Inc., Azusa, Calif.

[21] Appl. No.: 466,918

[22] Filed: Feb. 16, 1983

[51] Int. Cl.³ .......................... A61F 1/16; A61F 1/24
[52] U.S. Cl. ................................................. 623/6
[58] Field of Search .......................................... 3/13, 1

[56] References Cited

U.S. PATENT DOCUMENTS

| | | | |
|---|---|---|---|
| 4,159,546 | 7/1979 | Shearing | 3/13 |
| 4,174,543 | 11/1979 | Kelman | 3/13 |
| 4,242,760 | 1/1981 | Rainin | 3/13 |
| 4,244,060 | 1/1981 | Hoffer | 3/13 |
| 4,363,143 | 12/1982 | Callahan | 3/13 |
| 4,437,194 | 3/1984 | Hahs | 3/13 |

OTHER PUBLICATIONS

"The Intraocular Implant Lens Development and Results with Special Reference to the Binkhorst Lens", by M. E. Nordlohne, Second Edition, The Williams & Wilkins Co. (Book), Baltimore, 1975, pp. 16–23.
Style 115 Shepard Universal A/C IOL, Advertisement—American IOL International Intraocular Lenses, 15542 Grapham St., Huntington Beach, CA, Dec. 29, 1981.

*Primary Examiner*—Ronald L. Frinks
*Attorney, Agent, or Firm*—Bielen and Peterson

[57] ABSTRACT

An intraocular lens which is vaulted from contact with the iris utilizing an optical portion having an optical plane. The optical lens is positioned in the eye by connecting a first relatively rigid member to the optical portion. A first member attached to the optical portion and oriented away from the optical plane second part is connected to the first part and orients toward the optical plane in relation to the first part. A second relatively flexible member connects to the second part of the first member to form an appendage unit.

2 Claims, 2 Drawing Figures

U.S. Patent     Aug. 27, 1985     4,536,895
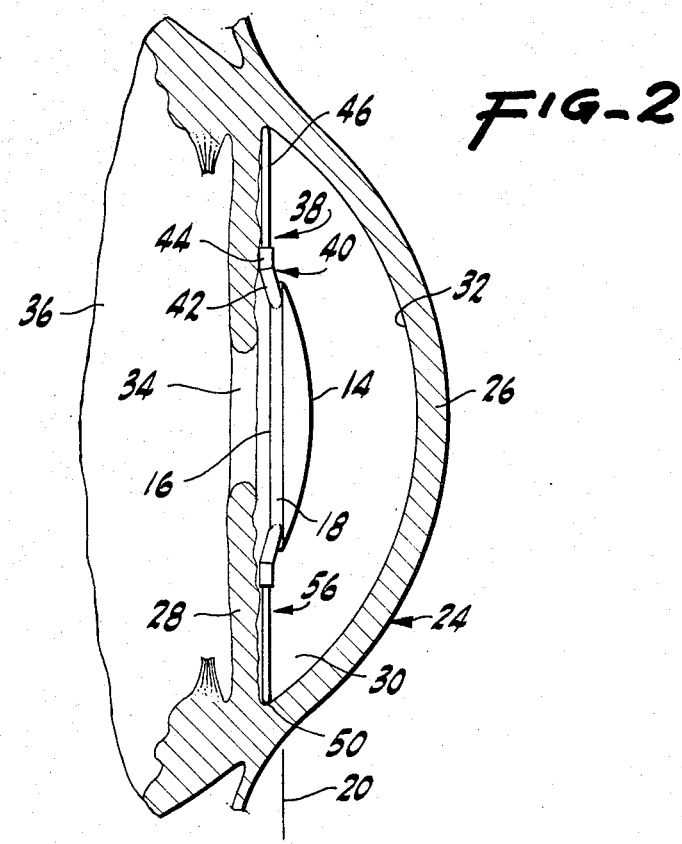
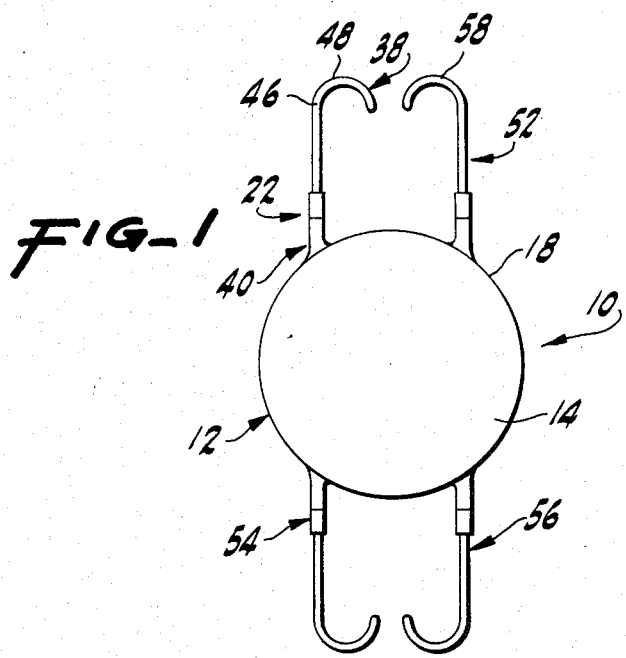

VAULTED INTRAOCULAR LENS

BACKGROUND OF THE INVENTION

The present invention relates to a novel intraocular lens which is specially useful for implantation in the eye adjacent the iris.

Implantation of intraocular lenses have become a standard procedure following cataract surgery. It is extremely important that the intraocular lens attain a state of fixation after implantation to prevent damage to the internal anatomy of the eye. For example an intraocular lens placed in the anterior chamber of the eye can cause serious damage to the endothelium which is the inside layer of the cornea. The endothelium cells do not regenerate after a mere touching of the same by any instrument or the like. Destruction of the endothelium layer will result blindness. Therefore, it is very important that anterior chamber fixation be permanent.

In addition, placing an intraocular lens next to the iris and in contact with the iris can cause iris chaffing. The pigmentation of the iris will be scraped off by an intraocular lens and remain on the surface of the intraocular lens in many cases. Also, an intraocular lens adjacent the iris may interfere with the opening and closing with the changing light conditions. This, of course, can also cause the intraocular lens to touch the endothelium resulting in a complex problem.

However, placement of an intraocular lens in an anterior chamber of the eye is in general a simplier procedure than placement of the intraocular lens in the posterior chamber after an extra-capsular or intra-capsular surgical procedure. The optical results by placement of the intraocular lenses in the anterior are very satisfactory in relation to those placed in the posterior chamber of the eye.

An intraocular lens which is simple to implant and remains fixed in the anterior chamber without damage to the cornea would be a great advance in the medical field of eye care.

SUMMARY OF THE INVENTION

In accordance with the present invention a novel and useful intraocular lens is provided which is especially useful for placement in the anterior chamber of the eye following cataract surgery.

The intraocular lens of the present invention employs an optical portion or lens portion which is used to perform the function of a natural lens. The optical portion may or may not include a haptic or other appurtenances for the handling and placement of the same.

The lens of the present invention also provides for means for positioning the optical portion in the eye. Such means may include a first relatively rigid member depending from the optical portion. The first member may be formed into a first part connected to the optical portion and oriented away from the optical plane. The second part of the first member connects to the first part and orients back toward the optical plane in relation to the first part. First and second parts may be formed into a smooth curve or be articulated as desired. The second part of the first member may lie substantially parallel to the optical plane of the optical portion.

A second relatively flexible member is connected to the first part of the first member. Thus the first and second members form an appendage unit such that the flexible member absorbs any force exerted by the anatomical portion of the eye while the first member maintains the optical portion to a planar movement. The relatively flexible member of the appendage unit may include an open loop design but may be formed into closed loops, complex loops and the like.

In addition, a second appendage unit maybe connected to the optical portion and lie adjacent or opposite the first appendage unit. Moreover, first and second and third and fourth appendage units maybe paired and connected to the optical portion.

It may be apparent that a novel and useful intraocular lens has been described.

It is an object of the present invention to provide an intraocular lens which achieves fixation and confines any movements of the optical portion of the lens to a plane.

It is another object of the present invention to provide an intraocular lens which maybe easily used in the anterior chamber of the eye and which maintains spacing between the cornea and iris. It is a further object of the present invention to provide an intraocular lens which possesses a degree of flexibility to absorb forces exerted thereupon without moving optical portion of lens outside a plane.

Another object of the present invention is to provide an intraocular lens which eliminates the dangers of endothelial touch and iris chaffing while implanted within the eye.

The invention possesses other objects and advantages especially as concerns particular characteristics and features thereof which will become apparent as the specification continues.

BRIEF DESCRIPTION OF THE DRAWINGS

FIG. 1 is a top plan view of the intraocular lens of the present invention.

FIG. 2 is a side view of the intraocular lens of the present invention implanted in the anterior chamber of the eye shown in section.

For a better understanding of the invention references made to the following detailed description which should be referenced to the hereinabove described drawings.

DESCRIPTION OF THE PREFERRED EMBODIMENTS

Various aspects of the present invention will evolve from the following detailed description of the preferred embodiments thereof which should be taken in conjunction with the hereinabove described drawings.

The invention as a whole is represented in the drawings by reference character 10. The intraocular lens device 10 includes as one of its elements an optical portion 12 which maybe fabricated of any optical material which is not reactive to human tissue, such as polymethylmethacrylate, and the like. Optical portion 12 includes surface 14, and surface 16. Edge portion 18 separates surfaces 14 and 16, FIGS. 1 and 2. Optical portion 12 lies in or is parallel to optical plane 20.

The intraocular lens of the present invention also includes means 22 for positioning optical portion 12 within eye 24. Turning to FIG. 1 it may be seen that eye 24 includes a cornea 26 and iris 28. The space between cornea 26 and iris 28 is referred to as the anterior chamber 30 of eye 24. Endothelium layer 32 is found on the inside of cornea 30. Pupil 34 leads to posterior chamber 36 where the natural lens has been removed as a result of an intra-capsular cataract surgical procedure.

Means 22 for positioning optical portion 12 in eye 24 may embrace an appendage unit 38, FIGS. 1 and 2. Appendage unit 38 is constructed such that a first relatively rigid member 40 is provided. First member maybe constructed of same material as optical portion 12 or other suitable material such as Dacron, Teflon, nylon and the like. Relatively rigid first member 40 maybe defined as having a first part 42 and a second part 44 connected thereto. First part 42 connects to optical portion 12 by welding or similar procedures or maybe formed integrally with optical portion 12. First part 42 orients away from optical plane 20. As shown in FIG. 2 first part 42 angles downwardly from edge 18 of optical portion 12. Second part 44 connects to first part 42 of relatively rigid first member 40 and orients back toward the optical plane 20. Second part 44, FIG. 2, is shown as being substantially parallel to or within optical plane 20. It should be noted that first and second parts 42 and 44 of relatively rigid member maybe formed to bend or curve continuously without articulation as shown in the drawings. Extending from and attached to first member 40 is a second relatively flexible member 46. Returning to FIG. 1 it may be seen that flexible member 46 takes the shape of an open loop. However flexible member 46 maybe formed into a closed loop, or a complex loop having a multiple points of fixation within the eye. Terminal end or edge portion 48 of member 46 is intended to contact eye tissue in the angle 50 within anterior chamber 30.

The embodiment shown in the drawings describes appendage units 52, 54 and 56 in addition to appendage units 38 hereinabove described. Appendage units 52, 54 and 56 are similarly constructed to appendage unit 38 with the exception of the relatively flexible members being turned or looped in various rotational directions, for example, second member 58 of appendage member 52 turns to the left while second member 46 turns to the right.

It may be apparent that optical portion 12 of lens 10 has been vaulted or raised above the surface of iris 28. Such vaulting prevents synache, iris chaffing, and other problems associated with the touching of iris 28 by foreign body. Although lens 10 is vaulted any forces on the ends of appendage units 38, 52, 54, and/or 56 will not move optical portion 12 upwardly toward endothelium layer 32. In other words, the provision of means 22 for positioning optical portion 12 within eye 24 vaults lens 10 as shown and also restricts any movements of optical portion 12 to optical plane 20 or a plane parallel to the same. The lens acts as a flat or a coplaner intraocular lens although it is the vaulted lens. This feature obviates many of the problems associated with touching the internal portions of the eye.

In operation the user inserts intraocular lens 10 within the anterior or posterior chamber of the eye as the case maybe following cataract surgery. Lens 10 will position itself within the eye and optical portion 12 will be confined to movement within a plane roughly parallel to iris 28. Flexible member 46 of appendage unit 38, as well as the remaining flexible members of appendage units 52, 54 and 56 will absorb the forces exerted by eye 24 following cataract surgery.

While on the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An intraocular lens for placement within an eye comprising:
    a. an optical portion having an optical plane;
    b. means for positioning said optical portion in the eye, said means comprising first and second appendage units, each of said first and second appendage units extending outwardly from and spaced from one another along one side of said optical portion, and third and fourth appendage units extending outwardly from and spaced from one another along another side of optical portion generally opposite said one side, each appendage unit including a first relatively rigid member depending from said optical portion, said first member including a first part connected to said optical portion and oriented away from said optical plane of said optical portion, said first part of said first member extending outwardly from said optical portion, said first member further including a second part connected to said first part and oriented, in relation to said first part, toward said optical plane said second part of said first member extending outwardly from said first part and from said optical portion, and, a second relatively flexible member connected to said second part of said first member and extending outwardly therefrom and outwardly in relation to said optical portion further than said first relatively rigid member, each relatively flexible member including an open loop defining a terminal end part for contacting eye tissue, said open loops of said first and second appendage units rotationally turned in opposite directions toward one another, and said open loops of said third and fourth appendage units rotationally turned in opposite directions toward one another.

2. The intraocular lens of claim 1 in which said second part of said first members of each appendage unit lies substantially parallel to the optical plane.

* * * * *